United States Patent
Senia et al.

(10) Patent No.: US 7,094,055 B2
(45) Date of Patent: Aug. 22, 2006

(54) ENDODONTIC REAMER AND A METHOD FOR MANUFACTURING ENDODONTIC REAMERS AND FILES

(76) Inventors: Steven Senia, 403 E. Ramsey, Suite 205, San Antonio, TX (US) 78216; Stuart Minica, 403 E. Ramsey, Suite 205, San Antonio, TX (US) 78216; E. Steve Senia, 403 E. Ramsey, Suite 205, San Antonio, TX (US) 78216; William L. Wildey, 1750 Cavender, Hurst, TX (US) 76054; Gene Rimmer, 6220 Culebra, San Antonio, TX (US) 78238; Ed D. Moore, 6220 Culebra, San Antonio, TX (US) 78238

( * ) Notice: Subject to any disclaimer, the term of this patent is extended or adjusted under 35 U.S.C. 154(b) by 300 days.

(21) Appl. No.: 10/099,107

(22) Filed: Mar. 15, 2002

(65) Prior Publication Data

US 2002/0182565 A1 Dec. 5, 2002

Related U.S. Application Data

(60) Provisional application No. 60/294,527, filed on May 30, 2001.

(51) Int. Cl.
*A61C 5/02* (2006.01)

(52) U.S. Cl. ....................................................... 433/102
(58) Field of Classification Search ................. 433/102, 433/141, 142, 143, 144, 145, 146, 147, 165, 433/166, 224, 225
See application file for complete search history.

(56) References Cited

U.S. PATENT DOCUMENTS

| 308,424 | A | * | 11/1884 | Morey | |
|---|---|---|---|---|---|
| 453,254 | A | * | 6/1891 | Bryant | |
| 3,832,779 | A | * | 9/1974 | Reynaud | |
| 4,187,611 | A | * | 2/1980 | Chan | 433/225 |
| 4,345,899 | A | * | 8/1982 | Vlock | 433/165 |
| 4,443,193 | A | | 4/1984 | Roane | 433/102 |
| 4,536,159 | A | | 8/1985 | Roane | 433/224 |
| 4,611,508 | A | | 9/1986 | Roane | |
| 4,661,061 | A | * | 4/1987 | Martin | 433/102 |
| 4,850,867 | A | * | 7/1989 | Senia et al. | 433/102 |
| 4,895,515 | A | * | 1/1990 | Axelsson | 433/166 |
| 4,934,934 | A | | 6/1990 | Arpaio | 433/102 |
| 5,017,137 | A | * | 5/1991 | Weissman | 433/102 |
| 5,215,461 | A | * | 6/1993 | Riazi | 433/224 |
| 5,464,362 | A | | 11/1995 | Heath | 451/48 |
| 5,527,205 | A | | 6/1996 | Heath | 451/48 |
| 5,628,674 | A | | 5/1997 | Heath | 451/48 |
| 5,655,950 | A | | 8/1997 | Heath | 451/48 |
| 5,762,541 | A | | 6/1998 | Heath | 433/102 |
| 6,186,788 | B1 | * | 2/2001 | Massad | 433/165 |

\* cited by examiner

*Primary Examiner*—Cary E. O'Connor

(57) ABSTRACT

An endodontic reamer and a method for manufacturing endodontic reamers and files, more specifically an endodontic reamer having a cylindrical shaft and a working portion extending forward from a removed end of the shaft. The working portion includes, typically, a pair of wedged shaped projecting sections that extend beyond the diameter of the shaft. Forward from the wedge shaped sections is a nose, typically non-cutting nose, that has a diameter of about equal to diameter of the shaft. There are typically two (2) wedge shaped sections projecting outward opposite one another. Applicant also provides a novel method for manufacturing an endodontic reamer, which consists of using a two piece mold and placing a wire blank between the mold, followed by forcing the mold together, under compression, against the wire blank, to deform the blank into the shape of the mold parts.

14 Claims, 8 Drawing Sheets

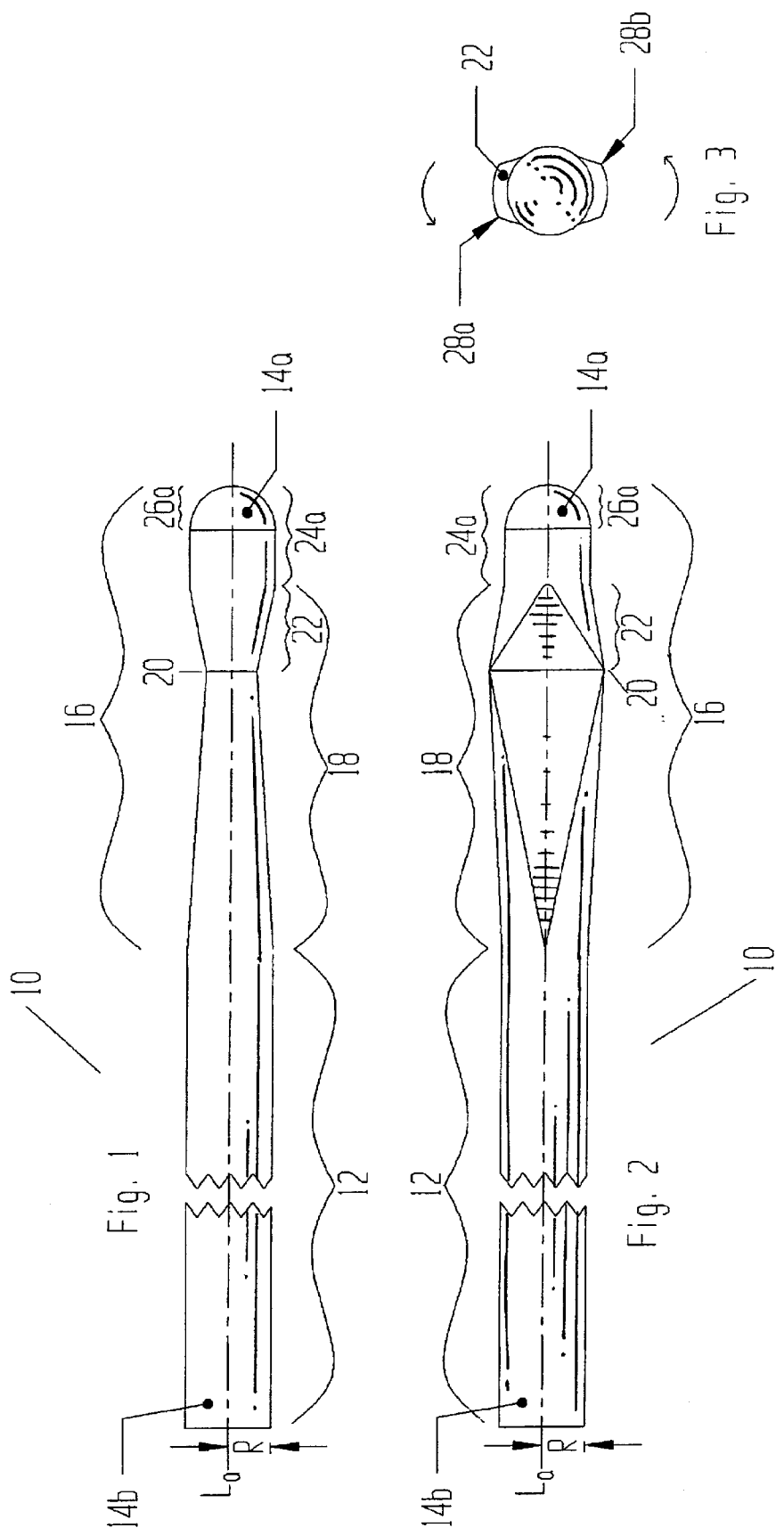

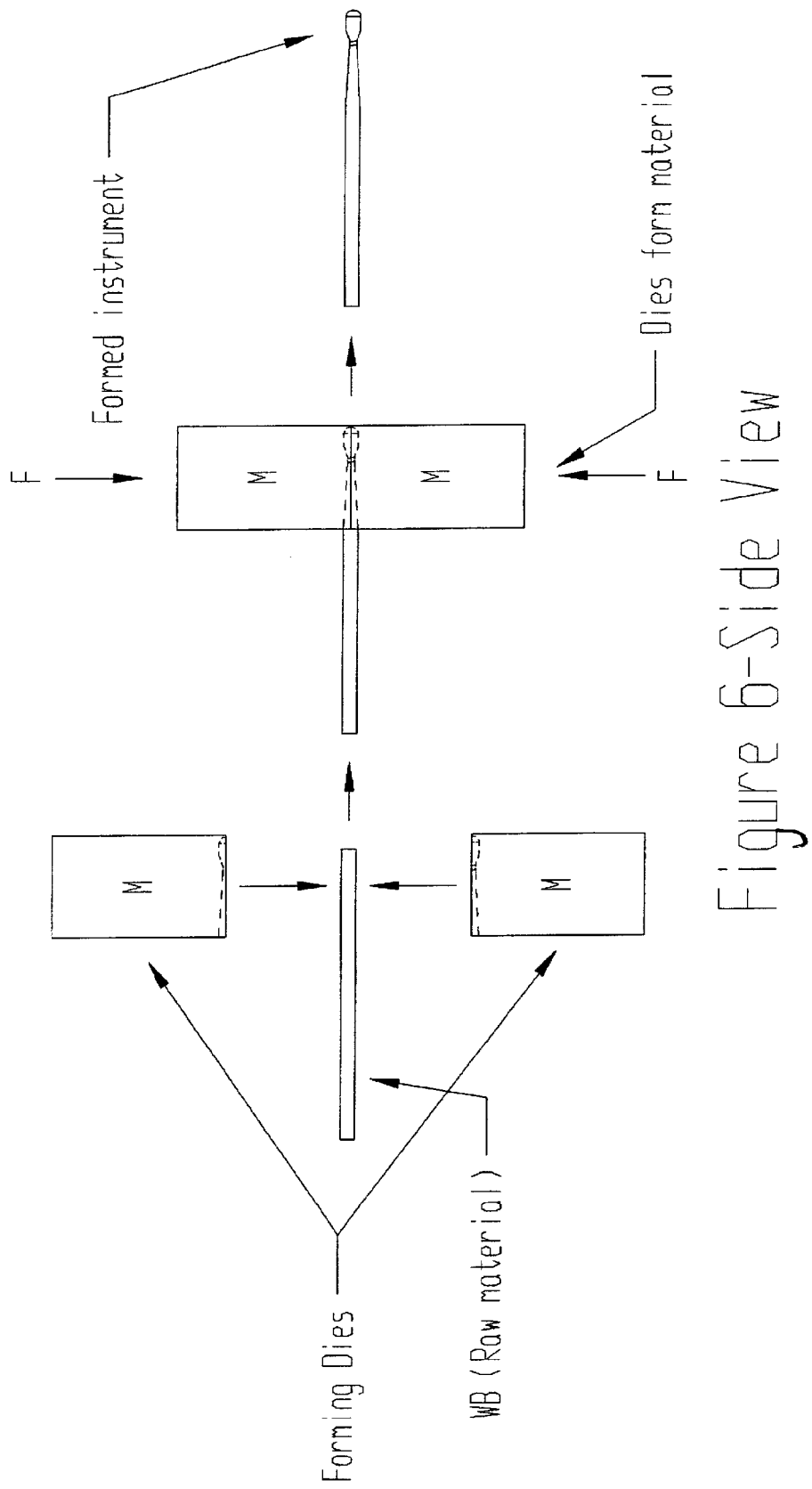

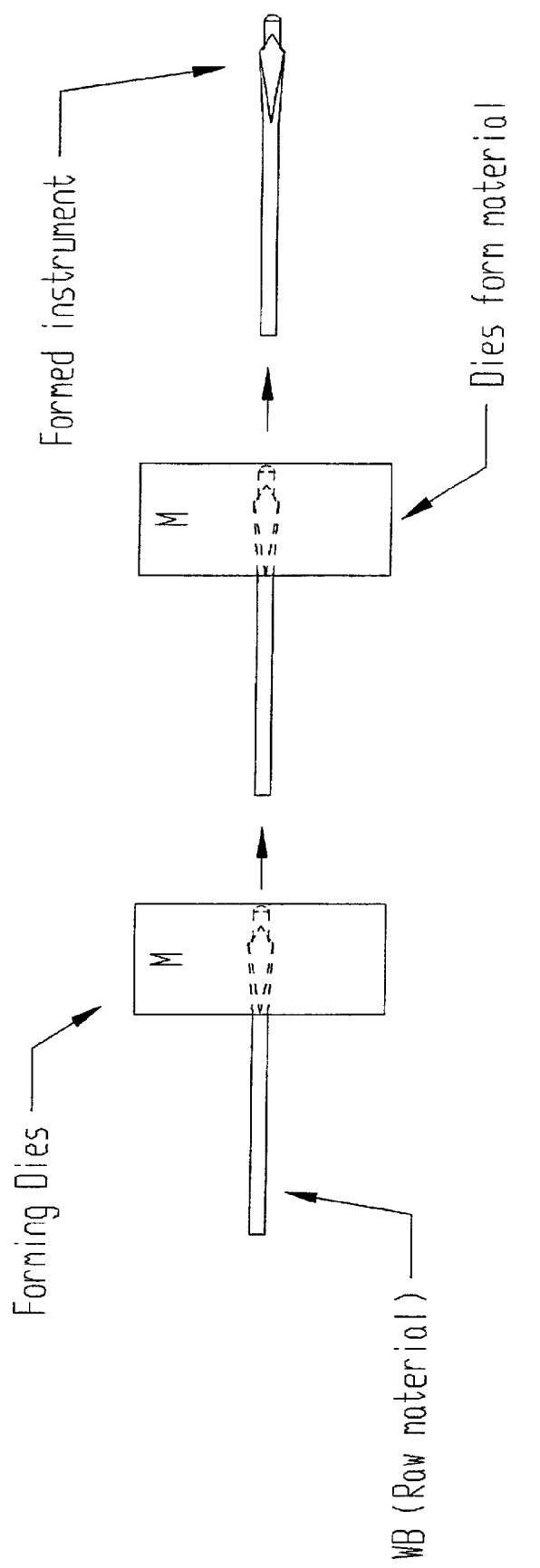

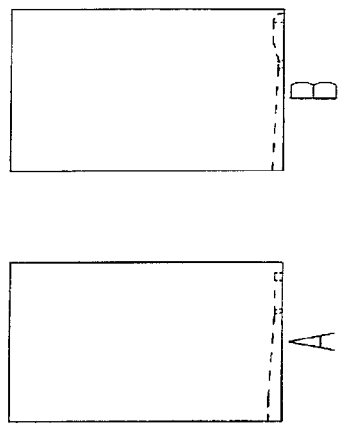
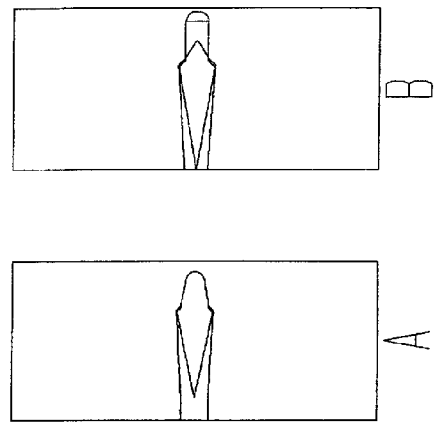

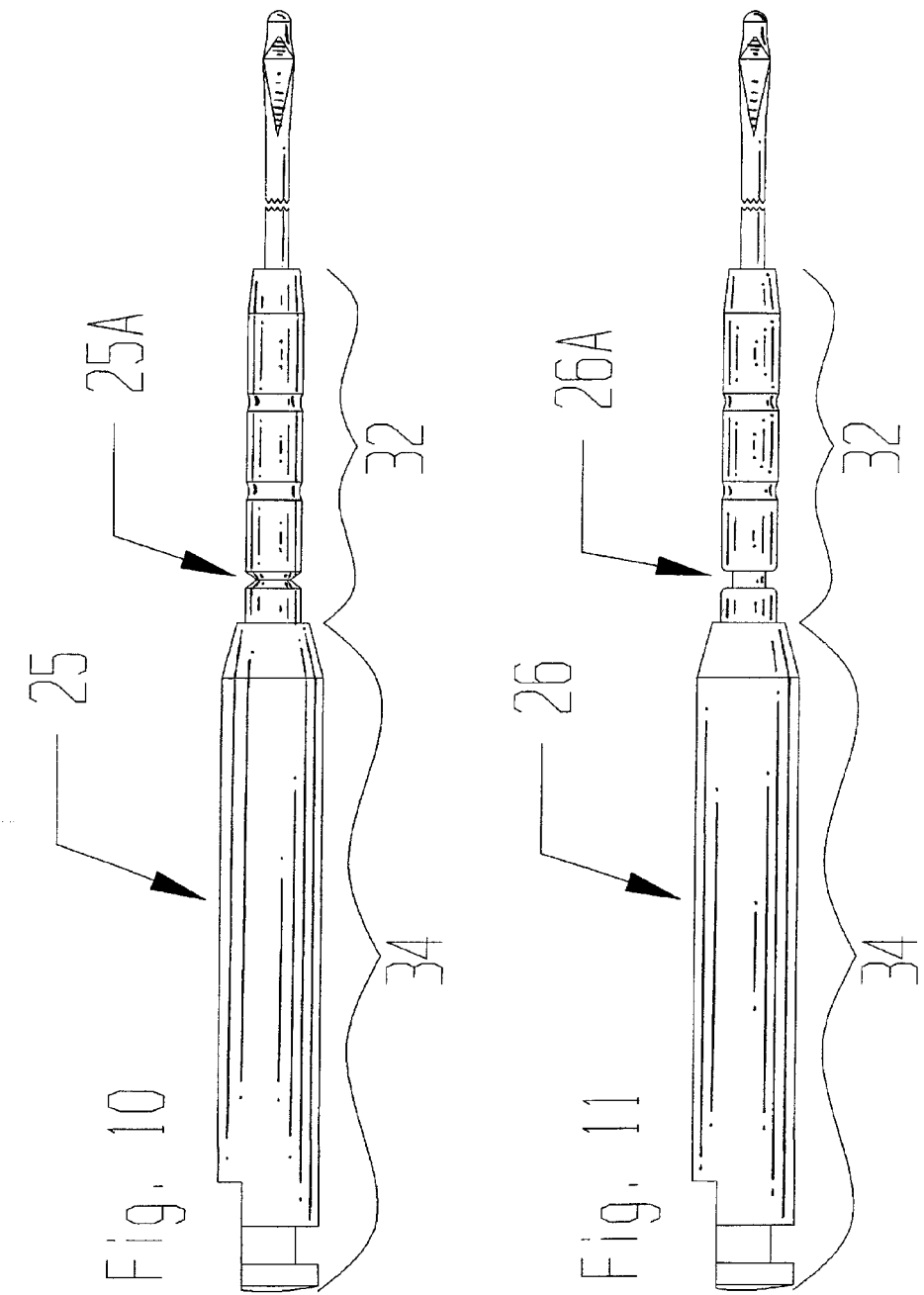

ENDODONTIC REAMER AND A METHOD FOR MANUFACTURING ENDODONTIC REAMERS AND FILES

This application is based on and claims priority from provisional patent application, Ser. No. 60/294,527, filed May 30, 2001.

FIELD OF THE INVENTION

An endodontic reamer and method for manufacturing endodontic reamers and files, more specifically a novel endodontic reamer comprised a longitudinal shaft having projecting wedges, and a novel method of forming an endodontic instrument with compression.

BACKGROUND OF THE INVENTION

The field of endodontics involves diseases of the tooth pulp, commonly known as a root canal, and typically requires the dentist to remove infected material from within the pulp of the tooth. The root canal itself is the space within the tooth that carries the blood supply into the tooth and contains the pulp. Within the root canal the pulp contains the nerve endings, which causes pain to warn when one bites down too hard on a hard object. From time to time, this space (the root canal) becomes infected and requires the dentist to clean (ream) out the root canal space in order to remove the pulp and/or other infected material. This cleaning consists of using a series of instruments to remove the pulp and infected material by enlarging and conically shaping the canal. Once cleaned and shaped, the space is sealed so that it does not become reinfected once again. It is the dentist's goal to provide complete cleaning by removing as much of the infected material as possible. The more infected material that is removed, the more likely the case has of being successful and thus the tooth saved. Otherwise, the tooth must be extracted and the space filled with a false tooth or treated by other means.

Endodontic reamers typically have helically wound cutting edges (blades). Rotation of the reamer allows the cutting blades to work within the root canal to cut dentin and remove infected material from the walls of the canal. Applicant has invented a novel endodontic reamer for effective cutting and removing of material that overcomes many limitations of the prior art of helically wound reamers. Applicant's novel endodontic reamer is comprised of a shaft having a longitudinal axis and wedge sections, not helically wound, with respect to the longitudinal axis.

Applicant provides a novel reamer for engagement at first end with a handle for manual manipulation or powered by a dental handpiece and a second end for engagement within the root canal of a patient requiring root canal therapy. Typically, the wedges are wider than the diameter of the shaft. Furthermore, the shaft is typically flexible as opposed to being rigid. This flexibility helps allow the reamer to stay centered within the root canal. The Applicant's wedges include forward and trailing portions that are typically at an angle oblique to the longitudinal axis. One or more cutting edges, which in a preferred embodiment may be straight, are typically provided—radiating outward around the shaft. A novel pilot tip guides the flexible shaft within the canal. The pilot tip can be cutting or noncutting.

The novel endodontic reamer's cutting blades can be typically very narrow and sharp; increasing it's cutting efficiency and reducing the number of instruments required by the dentist for treatment. Reducing the number of instruments also reduces the treatment time for both the dentist and patient. The cutting blades are typically made very thin, thus reducing the surface area contact of the blade with the root canal walls. These thin blades (typically from 0.01 mm to 1.00 mm thick preferably from 0.05 mm to 0.25 mm thick) also allow for more space for the previously cut material to reside before being irrigated and suctioned from the canal. When compared to prior art, this extra space helps reduce the loss of cutting efficiency that the cut material often causes by interfering with the cutting action of the blades. Thin blades increase cutting efficiency and reduce torsional stress on the shaft. Stress by torsion (twisting along the long axis of the shaft) is a primary cause of premature instrument breakage.

Applicant's reamer is manufactured by a novel method. This method includes using wire of the same diameter as the shaft of the finished product. The wire form may be cylindrical or tapered and be made from nonmetal or metals such as nitinol, stainless steel, and carbide steel. The wire provides the "blank" for the reamer. A second end of the wire, near the cutting portion is located and then swaged, coined, hot or cold formed, forged, pressed or otherwise subjected to mechanical compression to "flare" the second end such that it is flattened—thereby, having a width greater than the unflattened (round portion) of the wire and having a thickness narrower then the rounds portion in the other dimension. The leading edge of the flattened portion may be polished, machined, sheared or further formed into a sharp cutting edge.

In prior art, endodontic reamers have been ground into the desired shape. This grinding process is time consuming, requires many procedural steps and requires the use of very specialized, expensive machinery. This grinding process also generates imperfections and flawing on the surface of the finished work piece. These imperfections and flaws on the reamer's surface may lead to premature failure, increasing the risk to the patient, reducing the reamer's useful life and causing it to be more expensive for the dentist to use. This cost is thus passed onto the patient in the form of higher treatment costs. Thus for economic, rather than biological reasons, teeth are being unnecessarily extracted rather than saved.

Applicant's also provide for a novel process of manufacturing a dental instrument, including the novel reamer. Because the novel shaft is made without grinding the outside surface down to the desired the diameter, typical of prior art, less material is removed (wasted) and less material must be handled for disposal. Of significant importance, the surface of the shaft is not marred through the grinding process. The instrument's fatigue life is extended because the surface of the shaft is kept in its original state as when drawn into wire form. Finally, this simplified forming process allows for less complex and less expensive equipment to be used for manufacturing. The time to manufacture such an instrument is reduced. Less specialized equipment and the elimination of the time required to grind down the shaft reduces the cost of manufacturing such reamer.

Applicants also provide a novel handle, the handle for holding a file or reamer. Applicants' novel handle may include a shank. The shank is cylindrical and is designed to engage a file or a reamer. Applicants' novel handle includes a portion, typically along the shank, having a reduced diameter. This reduced diameter may take the shape of a groove (U-shaped) or a notch (V-shaped). By providing such a reduced diameter, Applicants provide a predictable break point, such that a file or reamer does not break in the tooth, but at the break point at the reduced diameter. In other words, rather than having a file or reamer break along a shaft or other part thereof, and thus be difficult to retrieve, Applicants' novel handle with a reduced diameter will break first and, will be far easier to retrieve from the tooth than a piece of a file or reamer that may be deep within the canal of the tooth.

OBJECTS OF THE INVENTION

It is the first object of Applicants' invention to provide a novel spade type drill, the spade drill having a working portion with a plurality of flutes or wedge shaped portions extending beyond the diameter of the shaft to define working portions, the working portions which cut the tooth.

It is a second object of Applicants' present invention to provide for a novel method of manufacturing a spade type reamer. The novel method includes compressing a cylindrical elonged wire blank or section between a pair of molds under compression to force the material to deform and take the shape of the molds.

It is a third object of Applicants' present invention to provide a novel handle, the handle for holding a file or a reamer, the handle including a portion which is grooved or notched to provide for a weakness or weak point at which the shaft may, under rotation, break if the cork on the shaft exceeds a predetermined value.

A BRIEF DESCRIPTION OF THE DRAWINGS

FIG. 3 presents an end elevational view of an alternate preferred embodiment of Applicants' present invention (looking towards the nose), as illustrated in FIGS. 1 and 2.

Figure 1A:
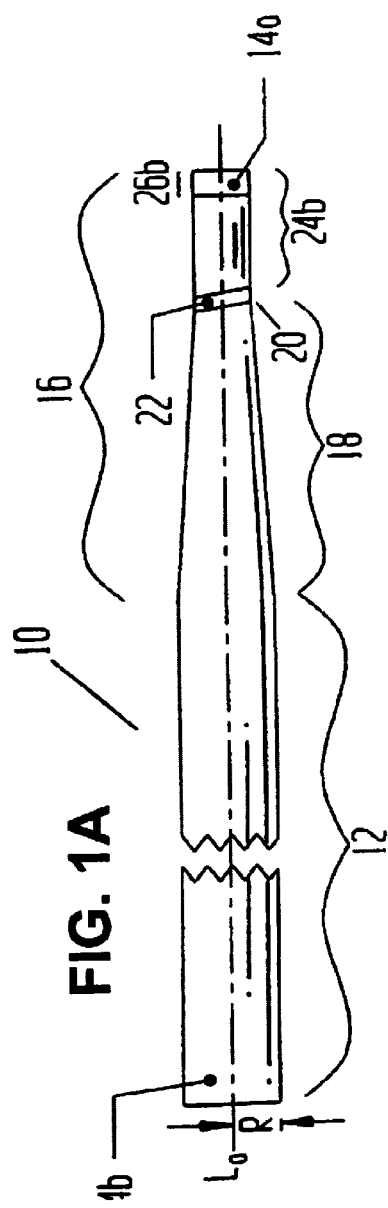
FIG. 1 illustrates a side elevational view of a preferred embodiment of Applicants' present invention (left side and right side views being identical), this view representing the view in FIG. 1 rotated 90 degrees.

FIG. 1A illustrates a side elevational view of an alternate preferred embodiment of Applicants' present invention (left side and right side views being identical).

Figure 2A:
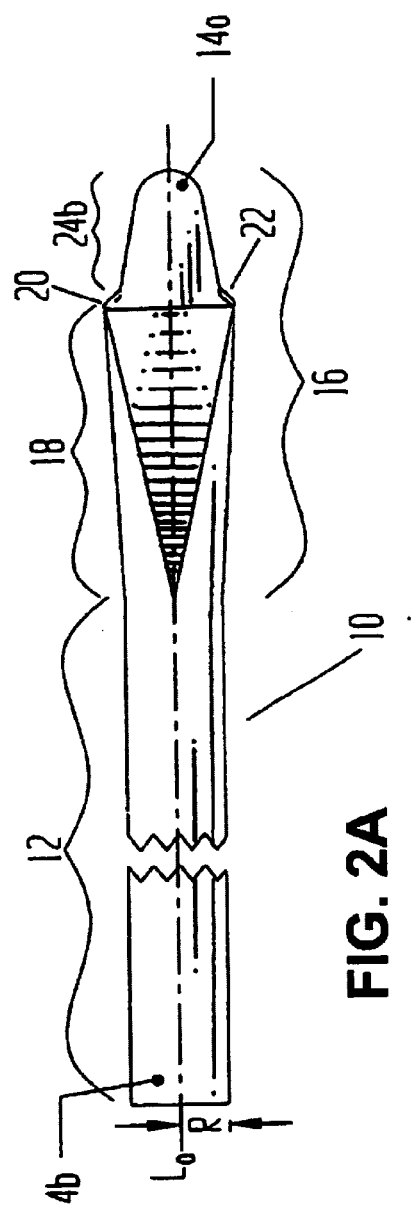
FIG. 2 illustrates a top view of a preferred embodiment of Applicants' present invention (top and bottom views being identical), as illustrated in FIGS. 1 and 2.

FIG. 2A illustrates a top view of an alternate preferred embodiment of Applicants' present invention (top and bottom views being identical), this view representing the view in FIG. 1 rotated 90 degrees.

Figure 3A:
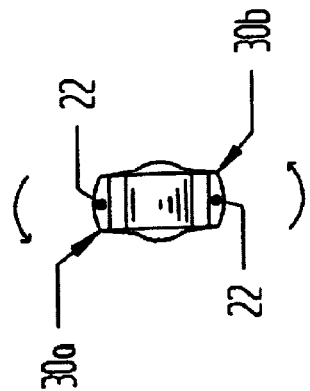

FIG. 3A presents an end elevational view of the alternate preferred embodiment of Applicants' present invention (looking towards the nose), as illustrated in FIGS. 1A and 2A.

Figure 4:
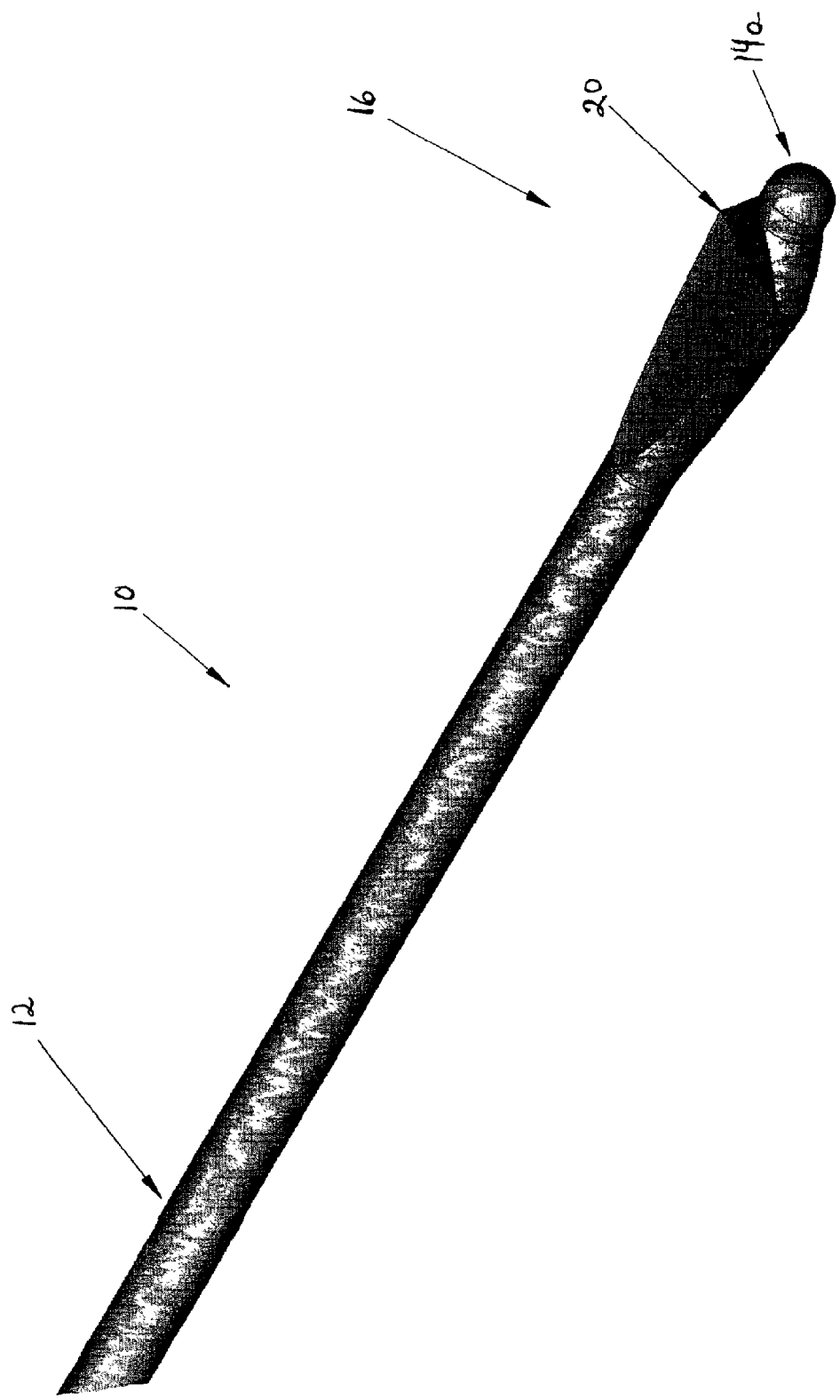

FIG. 4 is a perspective view of the preferred embodiment of Applicants present invention that is illustrated in FIGS. 1, 2 and 3.

Figure 5B:
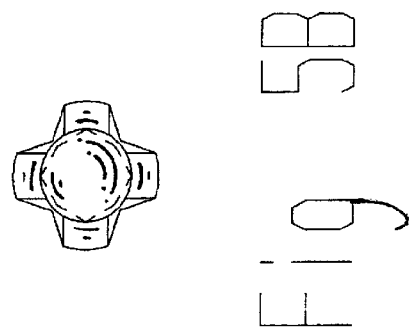
Figure 5A:
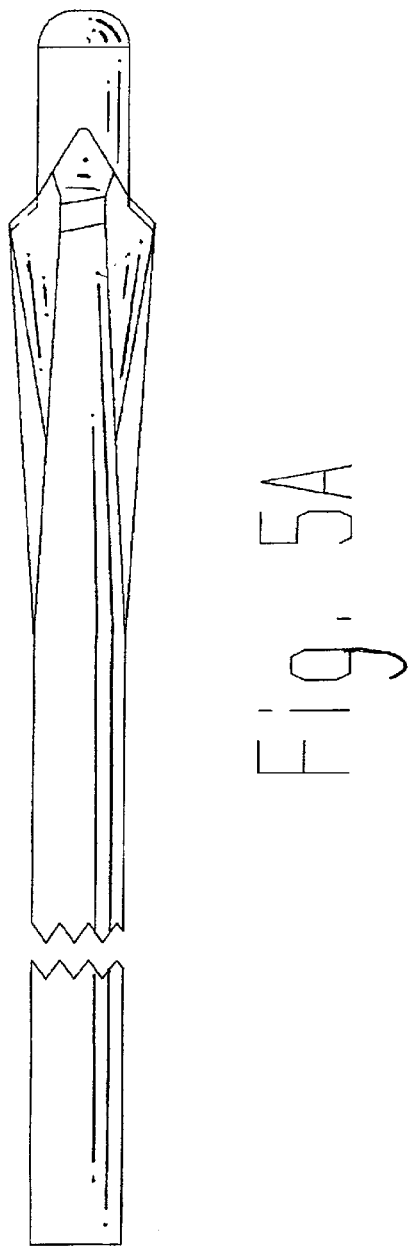

FIG. 5A represents a side elevational view of an alternate preferred embodiment of Applicants' present invention, having four fluted or wedge shaped projections radiating outward from the axis of the shaft.

FIG. 5B is an end view, looking into the nose, of the alternate preferred embodiment of Applicant's present invention that is illustrated in FIG. 5A.

FIG. 6 is a side view and FIG. 7 a top view of a novel method of manufacturing a dental instrument such as a file or reamer by compressive forces applied to a mold.

FIGS. 8 and 9 represent side and bottom views respectfully of two pairs of molds for manufacturing Applicants' novel reamer comprising a pair of opposed wedge shaped or fluted working portion, FIGS. 8A and 9A, and FIGS. 8B and 9B representing a preferred embodiment of mold pairs for manufacturing Applicants' novel reamers.

FIGS. 10 and 11 illustrate two alternate preferred embodiments of Applicants' handle, Applicants handle including means to break or separate at a predetermined torque.

DETAILED DESCRIPTION OF THE PREFERRED EMBODIMENT

FIGS. 1, 2 and 3, 1A, 2A and 3A represent alternate preferred embodiments of Applicant's novel reamer (10).

The referenced figures illustrate a novel reamer (10) comprised of a shaft portion (12) the shaft portion (12) having radius R and diameter D and a longitudinal axis $L_a$. Extending forward from the shaft portion of the reamer is a working portion (16). The working portion of the reamer typically includes that portion of the reamer that is actively involved in the cutting of the dentin.

The reamer has a first end (14a) and a second end (14b), the second end being adapted for the receipt of a handle (not shown) or for receipt into a motorized drive tool that will inpart a circular motion to the reamer. It is noted with reference to FIGS. 1 through 3 and 1A through 3A that the shaft ends and the working portion begins where the reamer begins to become narrower in a first view (See FIGS. 1 and 1A) and wider in a second view (See FIGS. 2 and 2A). This point is the beginning of the working portion, which working portion extends through to the first end of the reamer. With particular reference to FIGS. 1 and 2 and 1A and 2A note that both embodiments illustrate a projecting section of the working portion, the projecting section being that section which extends beyond radius R of the shaft as measured perpendicular to the longitudinal axis. Further note that the shaft has a longitudinal axis $L_a$ that is coincident with a longitudinal axis of the working portion. The embodiment set forth in the above referenced figures illustrates a reamer with a pair of oppositely located projecting sections. However, reference to FIG. 5 illustrates that there may in fact be more projecting sections, each with a working portion extending beyond the radius of the shaft.

Reference to the accompanying figures also illustrate that the shaft is substantially longer than the working portion and is flexible, providing for a working portion that may bend as it encounters a change in direction in the channel of the tooth. Typical lengths of shaft range from 1.0 mm to 100 mm (preferred 10 mm to 50 mm) and typical working portions range from 0.25 mm to 10 mm (preferred 1.5 mm to 3.0 mm), but the working portion is typically substantially shorter in length as compared to the length of the shaft (typically 3% to 25%). This allows for the requisite flexibility of the shaft.

The working portion may be seen to include a pair of opposed wedges (18) where in a first view (FIGS. 2 and 2A) the width first widens then reaches an apex (20), then narrows until it reaches the diameter of the shaft. The wedges (18) are seen, in a second view (FIGS. 1 and 1A) to first become thinner until they reach a minimum at apex (20) then thicker until they reach a thickness equal to the diameter of the shaft).

The working portion starts at the removed end of the shaft. The projecting sections or wedges 18 define an apex. Forward of the apex is a leading portion which extends forward of the apex and makes an angle of less than 90° with the longitudinal axis of the reamer. This is best seen in FIGS. 2 and 2A. The leading edge portion of the embodiment illustrated in FIGS. 1A, 2A and 3A has a rectangular outline. The shaft diameter may be between 0.01 mm and 3.00 mm and the length between 1.0 mm and 100.0 mm. The thickness at the apex may be between 0.009 mm and 2.99 mm.

Turning again to FIGS. 1, 2 and 3 and 1A, 2A and 3A it is seen that in views 2, 3, 2A, 3A the projecting portion reaches a maximum dimension at a widest point, apex 20 and, when viewed in FIGS. 1 and 1A a thinnest point or portion. Forward of the apex, Applicant's novel reamer includes a leading portion (22), the leading portion extending from the apex to nose 24*a*, (FIGS. 1 through 3) or nose 24*b*, (FIGS. 1A through 3A). The nose portion is equal to or less than the diameter of shaft (12) as measured in the longest dimensioned taken perpendicular to the longitudinal axis of the reamer. As mentioned above the longitudinal axis of the shaft and longitudinal axis of the working portion are coincident.

Applicant's embodiment illustrated in FIGS. 1 through 3 describes a nose (24*a*) that is circular in cross-section, the cross-section being taken perpendicular to the longitudinal axis, and a tip (26*a*) that is hemispherical. The embodiment illustrated in FIGS. 1A through 3A discloses a nose (24*b*) that is rectangular in cross-section, wherein the cross-sections taken perpendicular to the longitudinal axis of the reamer. Tip (26*b*) of nose (24*b*) is best described as hemi-cylindrical.

Turning back to the embodiment illustrated in FIGS. 1 through 3 it is noted that the leading portion (22) is shown to have a pair of primary cutting portions (28*a*) and (28B) when viewed in FIG. 3. FIG. 3 is the view that the canal of the tooth "sees" as the instrument works its way downward into the tooth. The arrow indicates the direction of rotation. If the direction of rotation were reverse portions (28*a*) and (28*b*) would shift to the opposite opposed corners. Compare the primary cutting portions (28*a*) and (28*b*) of the embodiment illustrated in FIGS. 1 through 3 with the primary cutting portions (30*a*) and (30*b*) in FIGS. 1A through 3A.

A section taken perpendicular to the longitudinal axis in the embodiment illustrated in FIGS. 1 through 3 on the leading portion would reveal edges where the same view taken in the embodiment illustrated in FIGS. 1A through 3A would illustrate a rectangle. Both instruments provide for effective cutting but testing is shown that when the rectangular nose embodiment encounters a channel narrower than the diameter of the shaft the nose portion may begin to cut aggressively. With the nose portion illustrated in FIGS. 1 through 3 (a circular nose) the nose does not having a cutting edge.

FIG. 4 is a perspective view of the embodiment of Applicants reamer that is illustrated in FIGS. 1, 2 and 3.

Please see FIGS. 6 and 7 for the novel method by which Applicant, manufacturers this or any other type of endodontic reamer or file. Many types of drills have been formed by methods such as those found in U.S. Pat. No. 5,816,807, the specifications of which are incorporated herein by reference. These patents disclose the manufacture of dental drills by removing or grinding material from the work piece. They do not disclose Applicant's novel method of swaging, stamping, coining, pressing forging or forming as set forth in FIGS. 6 and 7. FIGS. 6 and 7 illustrate a two-piece die or mold, M, and a force of other source of compression, F. The wire material or blank WB (which may be cut to length, as illustrated, or inserted between two pieces of the mold as unrolled from a spool), is placed between the two pieces of the mold. Compression force is applied as illustrated and deformation on the wire blank forces it into the shape of the finished piece. The process may require one or more "hits" from one or more directions to achieve the desired result.

The blank may be constructed from the following materials: nitinol, stainless steel, carbide steel or other steel, plastic, graphite, composites or any other suitable material. The blank can be of any cross sectional shape and have a parallel or tapered shape before forming. Some typical mold shapes are illustrated in FIGS. 8A and B, and 9A and B. Before forming, the dimensions of the blank may be as follows: 0.01 mm to 3 mm in diameter (preferred 0.10 mm to 1.00 mm) and 1 mm to 100 mm (preferred 10 mm to 60 mm) in length, or any other suitable dimension.

The novel method of manufacture allows dental endodontic reamers and files to be made more efficiently and economically. Prior art requires time-consuming processes with many manufacturing steps. Material is wasted which then must be disposed of properly. The surface of the blank is often marred during manufacturing, therefore the useful life is shortened making the instrument more costly for the dentist. Patients are losing their teeth to extraction rather than being saved because of the high cost of producing these instruments.

The novel manufacturing process requires compressive force and tool dies to form the desired shape. The process can form many pieces in a very short period of time. The machines required to form the parts are presses, four slide or multi-slides, or any custom press. These machines are commonly used in making many different parts for many different industries (but are not typically used in the dental industry to make reamers) and therefore they are relatively inexpensive to acquire, set up and maintain. With this new method of manufacturing, it is anticipated the cost of making a dental instrument such as a reamer will be one-fifth of the current cost to manufacture.

Please see FIGS. 10 and 11 for two preferred embodiments of a novel handle (25, 26) for this or any other type of endodontic reamer. The handle usually includes a body (34) at a proximal end and a shank (32) at a distal end, the shank cylindrical with a smaller diameter than the cylindrical body (34). The shank receives the reamer or file. The handle itself can be configured in many different shapes. Prior art describes reamers and files with handles attached for manual operation, or handles designed to fit into a dental handpiece for mechanical powered operation. Applicant's novel handles (25, 26) describe a groove (25A) ("V" shaped) or notch (26A) ("U" shaped) manufactured into the handle, typically along the shank (34). This notch (25A) or groove (26A) may be of various configurations, however; it serves as a predictable "breakpoint" when excessive torque is applied to the reamer or file when in use. The notch or groove defines walls having a diameter reduced from the walls immediately adjacent thereto on either side thereof; the notch or groove in the outer surface of the shank or body of the handle. Prior art, without this novel handle, may break unpredictably at the weakest point on the instrument. Unfortunately, this unpredictable break point often occurs deep inside the tooth making it virtually impossible for the dentist to retrieve the broken fragment. By knowing the minimum torsional load the instrument is able to withstand before breaking, and through careful engineering calculations based on the material of the handle, the depth of the notch or groove can be cut so that the handle itself will break before the reamer or file breaks. Breaking at this predictable point allows the instrument to be retrieved from the canal because it gives the doctor a "handle" to grasp and pull the broken fragment out of the root canal and because it breaks at a point easily, accessible instead of inside the canal.

The groove or notch will typically have a reduced diameter in the range of 25% to 75% of the diameter of the shank.

For example, if the shank diameter is 0.90 mm, the depth of the groove or notch will be in the range of 0.23 mm to 0.68 mm.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the inventions. The matter set forth in the foregoing description and accompanying drawings is offered by way of illustration only and not as a limitation. The actual scope of the invention is intended to be defined in the following claims when viewed in their proper perspective based on the prior art.

We claim:

1. A dental instrument having:
   an elongated flexible cylindrical shaft, the shaft having a longitudinal axis and a radius R, the shaft having a near end and removed end;
   a working portion, extending beyond removed end of the shaft and including a longitudinal axis coincident with the longitudinal axis of the elongated shaft, the working portion including at least one projecting section, each projecting section extending beyond a radius R and defining an apex, the projecting section including a leading portion extending forward of the apex and making an angle with the longitudinal axis of less than 90° and a trailing edge portion, the trailing edge portion extending rearward of the apex and making an angle of less than 90° with longitudinal axis, the projecting section having thickness T at the apex; and
   wherein each projecting section does not twist about the longitudinal axis of the working portion more than 359 degrees.

2. The dental instrument of claim 1 wherein shaft portion has a diameter of between 0.01 mm and 3.00 mm and a length between 1.0 mm and 100.0 mm.

3. The dental instruments of claim 1 wherein the working section has a thickness of between 0.009 mm and 2.99 mm.

4. The dental instrument of claim 1 wherein the leading portion has a rectangular shape.

5. The dental instrument of claim 1 wherein the leading portion is at least partially convex in cross-section.

6. The dental instrument of claim 1 wherein the dental instrument has at least two of the projecting sections, and the projecting sections include a pair of diametrically opposed projecting sections.

7. The dental instrument of claim 6 wherein the leading portion has a rectangular shape.

8. The dental instrument of claim 6 wherein the leading portion is at least partially convex in cross section.

9. The dental instrument of claim 6 where the projecting sections have a thickness between 0.009 mm and 2.99 mm.

10. The dental instrument of claim 6 comprised of one of the following: stainless steel, nitinol, plastic, composites, graphite and carbide steel.

11. The dental instrument of claim 6 wherein the shaft portion has a diameter of between 0.01 mm and 3.00 mm and length of between 1.0 mm and 100.0 mm.

12. A dental instrument comprising:
   an elongated flexible cylindrical shaft, the shaft having a longitudinal axis and a radius R, the shaft having a near end and removed end;
   a working portion, extending beyond removed end of the shaft and including a longitudinal axis coincident with the longitudinal axis of the elongated shaft, the working portion including at least one projecting section, each projecting section extending beyond a radius R and defining an apex, the projecting section including a leading portion extending forward of the apex and making an angle with the longitudinal axis of less than 90° and a trailing edge portion, the trailing edge portion extending rearward of the apex and making an angle of less than 90° with longitudinal axis, the projecting section having thickness T at the apex;
   wherein said shaft is not tapered; and
   wherein each projecting section does not twist about the longitudinal axis of the working portion more than 359 degrees.

13. The dental instrument of claim 12 wherein the leading portion is at least partially convex in cross-section.

14. The dental instrument of claim 12 wherein said dental instrument has at least two of the projecting sections, and the projecting sections include a pair of diametrically opposed projecting sections.

* * * * *